(12) United States Patent
Supplee et al.

(10) Patent No.: US 6,316,679 B1
(45) Date of Patent: Nov. 13, 2001

(54) TREATMENT OF A COMPOSITION COMPRISING A TRIMETHYLOLALKANE BIS-MONOLINEAR FORMAL

(75) Inventors: Carolyn Supplee; Jerry A. Broussard, both of Corpus Christi; Tobin J. Marks, Evanston; William E. Slinkard; Edwards G. Zey, both of Corpus Christi, all of TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/579,743

(22) Filed: May 26, 2000

Related U.S. Application Data

(63) Continuation-in-part of application No. 09/324,435, filed on Jun. 1, 1999, now Pat. No. 6,096,905.

(51) Int. Cl.[7] ............................ C07C 27/26; C07C 31/18; C07C 319/06
(52) U.S. Cl. ............................ 568/854; 568/853; 549/374
(58) Field of Search ............................ 549/374; 568/854, 568/853

(56) References Cited

U.S. PATENT DOCUMENTS 6,096,905 * 8/2000 Supplee et al. ...................... 549/374

\* cited by examiner

*Primary Examiner*—Samuel Barts
*Assistant Examiner*—Elvis O. Prize
(74) *Attorney, Agent, or Firm*—M. Susan Spiering

(57) ABSTRACT

A process for treating a composition containing a substantial proportion of trimethyflolpropane bis-monolinear formal (TMP-BMLF) or trimethylolethane bis-monolinear formal (TME-BMLF), e.g., a heavy ends residue obtained from the purification of a crude trimethylolpropane (TMP) or trimethylolethane (TME) product, wherein the composition is contacted at an elevated temperature with a strong acid catalyst, e.g., methanesulfonic acid, to produce a composition containing significantly increased amounts of TMP and trimethylolpropane monocyclic formal (TMP-MCF) or TME and trimethylolethane monocyclic formal (TME-MCF) respectively. Also disclosed is a process for reacting TMP-MCF or TME-MCF, either in substantially pure form or as present in the light ends overhead stream obtained in a finishing treatment of crude TMP or TME, with a monohydric or dihydric alcohol, e.g., ethylene glycol, in the presence of a strong acid catalyst to obtain additional TMP or TME and an acetal by-product, e.g., 1,3-dioxolane; and a process for directly reacting the TMP-BMLF or TME-BMLF present in a composition, e.g., the heavy ends residue obtained in the purification of TMP or TME, with a monohydric or dihydric alcohol, e.g., ethylene glycol, in the presence of a strong acid to obtain additional TMP or TME and an acetal by-product, e.g., 1,3-dioxolane.

34 Claims, No Drawings

TREATMENT OF A COMPOSITION COMPRISING A TRIMETHYLOLALKANE BIS-MONOLINEAR FORMAL

CROSS-REFERENCE TO RELATED APPLICATION

This application is a continuation-in-part of application Ser. No. 09/324,435 filed Jun. 1, 1999 now 6,076,905.

BACKGROUND OF THE INVENTION

1. Field of the Invention

The invention relates to a novel process for treating a composition comprising a trimethylolalkane bis-monolinear formal such as that obtained as a heavy ends residue from the purification of a crude trimethylolalkane product, to obtain useful compounds.

2. Description of the Related Art

Trimethylolpropane (TMP) and trimethylolethane (TME) are well-known chemical commodities used as intermediates in the production of a wide variety of products, e.g., varnishes, alkyd and polyester resins, synthetic drying oils, urethane foams and coatings, silicone lube oils, lactone plasticizers, textile finishes, surfactants, epoxidation products, etc. TMP and TME are made by reacting one mole of n-butyraldehyde or propionaldehyde respectively with an amount in excess of 3 moles of formaldehyde in an aqueous medium and in the presence of an alkaline condensation agent. However, these conditions result in the formation of not only TMP or TME, but also various higher boiling impurities. Thus it is necessary to subject the crude TMP or TME product obtained from the reaction to a purification process including distillation and solvent extraction steps, not only to separate relatively pure UMP or TME from excess formaldehyde, water, and basic condensation agent, but also from the higher boiling impurities.

A critical step in the purification process for obtaining relatively pure TMP or TME from the crude product of the reaction is a vacuum distillation or "flashing" of the bulk of the TMP or TME produced in the reaction, which is thus removed as a vapor from the higher boiling impurities remaining behind as a liquid heavy ends residue. While the residue may still contain some TMP or TME, the percentage of such desirable compound is fairly low and is difficult to recover economically. Furthermore, several of the high boiling impurities produced by the reaction in fairly large amounts have only limited commercial value. Thus, any expedient for treating the heavy ends residue, or any compound present in such residue in large amount, so as to convert at least a portion of such compound to TMP or TME and/or other more valuable compounds, would be very desirable.

U.S. Pat. No. 3,076,854 issued Feb. 5, 1963 to Klein, discloses the purification of crude TMP product by a process comprising extracting the reaction liquor with a water immiscible solvent for TMP, e.g., n-butanol or amyl alcohol, subjecting the extract to further extraction with water to obtain a re-extract containing TMP contaminated with metal formate and polyhydric by-products; separating the aqueous re-extract from the stripped solvent, heating the contaminated TMP with methanol or other lower alkanol and a mineral acid to convert the metal formate to a salt of the added acid, and further treating the aqueous TMP re-extract with an acidic cation-exchange resin to remove metal ions from the solution. British Patent No 1,290,036 discloses a process for removing trimethylpropane monomethyl formal from a crude TMP product by treating the product with a sulfonic acid cation exchange resin. The trimethylolpropane monomethyl formal decomposes to form trimethylolpropane monocyclic formal and methanol.

German Democratic Republic Patent No. 142184 discloses a process for the recovery of TMP from higher boiling residues comprising adding water and methanol to the residues such that they contain at least 15 wt. % of water or 10–40 wt. % of methanol, pretreating the residues with a cation exchange resin to remove traces of condensation agent contained in the residues, treating the residues under distillation conditions with a highly acidic, highly crosslinked cation-exchange resin with a polystyrene base, and recovering the TMP formed by conventional separation means.

BRIEF SUMMARY OF THE INVENTION

As part of the invention disclosed herein, it has been discovered that a major proportion of the heavy ends residue obtained after removing the bulk of the TMP or TME, excess formaldehyde, water, and basic condensation agent, is a trimethylolalkane bis-monolinear formal having the formula,

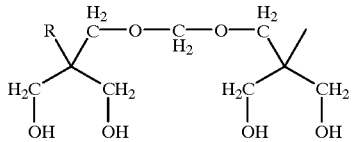

where R is ethyl in the case of trimethylolpropane bis-monolinear formal (TMP-BMLF) CA Index Name 1,3-Propanediol, 2,2'-[methylenebis(oxymethylene)]bis[2-ethyl-], CAS No. [93983-16-5] or methyl in the case of trimethylolethane bis-monolinear formal (TME-BMLF) CA Index Name 1,3-Propanediol, 2,2'-[methylenebis(oxymethylene)]bis[2-methyl-], CAS No. [636073-72-5]. Thus, in accordance with the broadest aspect of the invention, a composition comprising a substantial percentage, e.g., at least about 40 wt. %, of TMP-BMLF or TME-BMLF, no more than about 5 wt. % of water, and no more than about 0.5 wt. % of methanol, all percentages based on the total weight of the composition, is contacted with a strong acid catalyst at an elevated temperature and a sufficient period of time to convert a significant amount of said TMP-BMLF or TME-BMLF to TMP or TME and the corresponding trimethylolalkane monocyclic formal having the following formula,

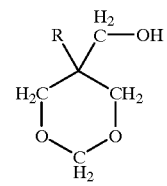

where R is ethyl in the case of trimethylolpropane monocyclic formal (TMP-MCF) CA Index Name 1,3-Dioxane-5-methanol, 5-ethyl, CAS No. [5187-23-5] or methyl in the case of trimethylolethane monocyclic formal (TME-MCF) CA Index Name 1,3-Dioxane-5-methanol, 5-methyl, CAS No. [1121-97-7]. The additional TMP and TMP-MCF or TME and TME-MCF produced by the process have considerably greater value than the TMP-BMLF or TME-BMLF consumed. In many instances the composition treated is a heavy ends residue obtained from a crude TMP or TME product in the course of a purification treatment after the bulk of water, excess formaldehyde, basic condensation agent, and purified TMP or TME have been separated.

DETAILED DESCRIPTION OF THE INVENTION

The composition subjected to the acid treatment of this convention will in many instances contain, for example, at least about 10 wt. %, preferably at least about 20–30 wt. % of TMP-BMLF or TME-BMLF, generally anhydrous to no more than about 5 wt. %, preferably no more than about 1.0 wt. % of water, and no more than about 0.5 wt. %, preferably no more than about 0.1 wt. % of methanol. In addition, the composition being treated will usually contain no more than about 5 wt. %, preferably no more than about 0.6 wt. % of any compound in free form having an atmospheric boiling below that of water, such as formaldehyde. The composition is contacted at an elevated temperature, e.g., about 30° C. to about 300° C. preferably about 90° C. to about 220° C., with a strong acid catalyst, for a period of time, e.g., of about 2 to about 8 hours, preferably about 1 to about 6 hours, sufficient to convert a significant amount of the TMP-BMLF or TME-BMLF to TMP and TMP-MCF or TME and TME-MCF respectively.

Any strong acid can be used as a catalyst for the process of the invention. While such acid may be an inorganic acid such as sulfuric or phosphoric, it is preferred in most instances to employ an alkanesulfonic acid such as methanesulfonic acid, an arylsulfonic acid such as toluenesulfonic acid, or a sulfonated cation-exchange resin in acid form, e.g., a sulfonated polystyrene-based cation exchange resin. The amount of acid may vary widely, but is often in an amount such that the acidity of conversion reaction is in the range, for example, equivalent to the acidity contributed by the strong acid, less than about 15 wt. %, preferably about 0.3 to about 1.3 wt. %.

Generally a strong acid is added in sufficient amount to result in a pH range of the reaction of less than about 4, and preferably between about 2 and 3, purified BMLF has been found to optimally convert to TMP at about 102° C., pH of about 2.35 in about 4 hours.

As suggested previously, a small amount of water under 5 wt. % may be present in the composition subjected to the acid treatment of this invention. Furthermore, an additional amount of water is produced by the conversion of TMP-BMLF or TME-BMLF to TMP-MCF or TME-MCF respectively. Although not necessary to obtain the advantages of the process, it may be desirable in some instances to keep the amount of water at a lower level than would ordinarily occur. For this purpose a minor amount, e.g. less than about 15 wt. % preferably less than about 10 wt% based on the weight of the composition, of a compound which forms a low boiling azeotrope with water and is substantially immiscible with any of the components of the composition, may be added prior to the initiation of the reaction. Such compound is preferably a hydrocarbon, e.g., cyclohexane, toluene or benzene.

As stated, the process of the invention results in the conversion of a significant amount of the TMP-BMLF or TME-BMLF in the initial composition to TMP and TMP-MCF or TME and TME-MCF respectively. For example, in the case of TMP, it has been found that the product resulting from the acid treatment of the process of the invention may contain at least about 5 wt. %, more TMP-MCF than was present in the initial composition subjected to such acid treatment, based on the weight of the total composition.

Conversely, for example, the amount of TMP-BMLF in the product was found to be reduced by at least about 70 wt. %, of that in the initial composition based on the weight of TMP-BMLF before the acid treatment.

As described previously, the composition subjected to the acid treatment of this invention will in many instances be obtained as a heavy ends residue from a process for producing TMP or TME by reaction of n-butyraldehyde or propionaldehyde with formaldehyde in an aqueous system in the presence of a basic condensation agent such as sodium hydroxide. Such a residue is obtained from the purification of the product of the reaction including the following steps: 1) removal of excess formaldehyde; 2) removal of water; 3) separation of TMP or TME and higher boiling impurities from the liquid being purified, and the basic condensation agent and, 4) heating the crude TMP under vacuum to flash off and recover the TMP or TME having a high degree of purity. The remaining residue is the heavy ends residue containing high boiling impurities contemplated for acid treatment under this invention.

When the composition being treated is the heavy ends residue from a TMP process as described previously, such composition usually contains, in addition to TMP-BMLF, TMP in an amount, e.g. less than about 60 wt. %, typically often about 8 to about 20 wt. %; less than about 15 wt. %, typically about 7 to about 10 wt. % of di-trimethylpropane (Di-TMP). The amount of TMP-MCF present in said heavy ends residue is generally lower than the latter compounds, usually less than about 0.1 wt. % and often non-detectable.

In accordance with another aspect of the invention, TMP-MCF or TME-MCF in the composition resulting from the process of the invention is subjected to a transalcoholysis reaction with an excess of a monohydric or dihydric alcohol, e.g., containing 1 to about 6 carbon atoms, at an elevated temperature, e.g., about 30° C. to about 300° C., in the presence of an acid catalyst, e.g., any of the same acids disclosed previously in connection with the acid treatment of TMP-BMLF or TME-BMLF, to produce additional TMP or TME and an acetal by-product which is often commercially desirable. Thus, for example, the TMP-MCF or TME-MCF in the composition resulting from the acid treatment of the invention may be reacted with excess methanol to produce additional TMP or TME and methylal, useful as a solvent, in organic synthesis, in perfumes, in adhesives, etc., while TMP-MCF or TME-MCF may be reacted with excess ethylene glycol to produce additional TMP or TME and 1,3-dioxolane, useful as low-boiling solvent and extractant for oils, fats, waxes, dyes and cellulose derivatives.

In addition to their use an intermediate in transalcoholysis reactions to produce additional TMP or TME and other useful compounds, TMP-MCF and TME-MCF may be used to produce useful products by other reactions. Thus, as disclosed in U.S. Pat. Nos. 4,076,727; 4,207,155 and 4,876, 368, acrylate and methacrylate esters of TMP-MCF and TME-MCF may be prepared which are useful as reactive monomers in the preparation of coating compositions, plastic films, fibers, plastic coatings and, in particular, as diluents in various unsaturated systems, especially ultraviolet curable coating compositions.

The following examples further illustrate the invention. Small amounts of water were removed from the system utilizing cyclohexane as an azeotroping agent.

EXAMPLES 1 AND 1A

In Example 1, a round-bottom flask, equipped with an overhead stirrer, Dean Stark trap with condenser, and a heating system, was charged at ambient temperature with 91.30 grams of a previously analyzed, heavy ends residue obtained from the purification of a crude TMP product as described hereinbefore, 12.53 grams of cyclohexane, and 0.25 grams of methanesulfonic acid as a catalyst. The charge was heated to 98° C. over a period of 90 min., and a sample of product withdrawn and analyzed.

In Example 1A, the procedure of Example 1 was repeated, except that the charge was heated to 110° C. over a period of 275 min.

The compositions of the initial heavy ends residue feed and the treated compositions of Examples 1 and 1A in terms of weight percentages of the most significant components based on the weight of the total composition are shown in Table I.

TABLE I

| Component | Initial Feed | Treated Ex. 1 | Composition Ex. 1A |
|---|---|---|---|
| TMP-MCF | 0.05% | 27.77% | 25.64 |
| TMP | 22.67% | 36.31% | 34.13 |
| TMP-acetate | Undetected | Undetected | 0.15 |
| Di-TMP | 7.65% | 4.39% | 3.54 |
| TMP-BMLF | 41.74% | 0.55% | Undetected |
| DMB | 0.11% | 8.86% | 7.66 |
| MMB | 5.99% | 0.31% | 0.25 |

EXAMPLE 2

The procedure of Example 1 and 1A was followed, except that the initial charge was 462.00 g of heavy ends residue, 69.19 g of cyclohexane and as catalyst, 69.19 g of sulfonated acrylic-polystyrene based cation exchange resin in acid form sold as "Amberlyst 36 (dry)" by Rohm and Haas Co. In employing the solid resin catalyst of this example, the experimental apparatus was modified as follows: The resin was weighed and poured into a "mesh-wire stainless steel basket" which was attached to the stirring shaft. This basket was shaped like an "X" and had four components which were filled with resin. Once filled, the basket was connected to the overhead stirrer motor. Each side of the "basket" had a length of ~7.5 cm, a width of 4 cm and a depth of 1.5 cm and was made using wire with ~42 mesh size. The design and use of the basket allowed heavy ends residue to have intimate contact with the solid acid resin as well as preventing degradation of the solid catalysts due to "grinding" from the stirrer blade.

The charge was heated from 25 to 99.6° C. in 190 min. and kept between 99.5° C. and 99.8° C. for an additional period of 180 min. (total heating time 370 min.). The composition of withdrawn samples at various time intervals and temperatures are shown in Table II. "N/D" means non-detectable.

TABLE II

| Time (min) | Temp. ° C. | TMP-MCF | TMP | Di-TMP | TMP-BMLF | H$_2$O |
|---|---|---|---|---|---|---|
| 0 | 25 | N/D | 10.04 | 7.11 | 58.56 | 0.10 |
| 40 | 83.4 | 0.42 | 10.85 | 7.00 | 52.90 | 0.25 |
| 105 | 95.5 | 23.28 | 26.87 | 4.23 | 5.60 | 0.79 |
| 190 | 99.6 | 32.77 | 28.58 | 4.46 | 0.61 | 0.65 |
| 250 | 99.8 | 32.89 | 28.43 | 4.18 | 0.56 | 0.53 |
| 320 | 99.6 | 32.84 | 28.46 | 4.06 | 0.56 | 0.53 |
| 370 | 99.5 | 31.36 | 27.19 | 3.88 | 0.53 | 0.53 |

EXAMPLE 3

The procedure of Example 2 was followed, except that the initial charge consisted of 709.43 g of heavy ends residue, 96.00 g of cyclohexane and as catalyst, 67.35 g of sulfonated acrylic-polystyrene based cation exchange resin in acid form sold as "Amberlyst 35 (dry)" by Rohm Haas Co.

The charge was heated from 25° C. to 95.7° C. in 295 min. and the composition of withdrawn samples at various time intervals and temperatures are shown in Table III.

TABLE III

| Time (min) | Temp. ° C. | TMP-MCF | TMP | Di-TMP | TMP-BMLF | H$_2$O |
|---|---|---|---|---|---|---|
| 0 | 25 | N/D | 10.04 | 7.11 | 58.56 | 0.10 |
| 38 | 73.9 | N/D | 10.38 | 7.31 | 57.54 | 0.28 |
| 72 | 83.3 | 14.81 | 25.07 | 4.05 | 11.02 | 1.39 |
| 130 | 91.6 | 34.06 | 30.64 | 4.81 | 0.63 | 1.03 |
| 175 | 93 | 33.24 | 30.03 | 4.52 | 0.61 | 1.25 |
| 245 | 94.3 | 33.65 | 29.77 | 4.20 | 0.62 | 0.63 |
| 295 | 95.7 | 33.5 | 30.02 | 4.30 | 0.62 | 0.89 |

EXAMPLE 4

The procedure of Example 1 was followed, except that the initial charge consisted of 157.85 grams of heavy ends residue, 24.58 grams of cyclohexane, and, as catalyst, 0.86 gram of a modified toluenesulfonic acid sold as "Witco TX Acid" by Witco Chemical Corp., containing 1.0 wt. % of moisture and 2.0 wt. % of sulfuric acid, and having a melting point under 15° C., a specific gravity at 254° C. of 1.30 and an acid number of 330. The charge was heated from 25° C. to 200° C. in 182 min. and the compositions of withdrawn samples at various time intervals and temperatures are shown in Table IV.

TABLE IV

| Time (min) | Temp. ° C. | TMP-MCF | TMP | Di-TMP | TMP-BMLF | H$_2$O |
|---|---|---|---|---|---|---|
| 0 | 25 | N/D | 10.04 | 7.11 | 58.56 | 0.10 |
| 60 | 100 | 31.39 | 29.62 | 5.07 | 0.78 | 0.20 |
| 75 | 112 | 32.65 | 30.80 | 5.14 | 0.65 | 0.10 |
| 80 | 127 | 32.37 | 31.31 | 5.06 | 0.71 | 0.14 |
| 85 | 143 | 32.28 | 32.22 | 4.55 | 0.62 | 0.11 |
| 98 | 160 | 33.00 | 32.13 | 4.51 | 0.80 | 0.27 |
| 108 | 175 | 34.06 | 31.72 | 4.38 | 0.80 | 0.38 |
| 120 | 185 | 36.61 | 27.89 | 3.76 | 0.82 | 0.45 |
| 151 | 190 | 41.66 | 20.45 | 2.58 | 0.75 | 0.37 |
| 182 | 200 | 46.13 | 17.43 | 2.36 | 0.84 | 0.34 |

EXAMPLE 5

The procedure of Example 4 was followed, except that the initial charge consisted of 186.54 grams of heavy ends residue, 24.82 grams of cyclohexane and 0.92 grams of modified toluenesulfonic acid catalyst. The charge was heated to 121° C. in 138 minutes and kept between 121 ° C. and 133° C. for an additional 265 min. for a total heating time of 403 min. The composition of withdrawn samples at various time intervals and temperatures are shown in Table V.

TABLE V

| Time (min) | Temp. ° C. | TMP-MCF | TMP | Di-TMP | TMP-BMLF | H$_2$O |
|---|---|---|---|---|---|---|
| 0 | 25 | N/D | 10.04 | 7.11 | 58.56 | 0.10 |
| — | 40 | 2.09 | 17.66 | 6.23 | 39.4 | 0.81 |
| 11 | 50 | 11.91 | 25.97 | 4.13 | 11.61 | 0.62 |

TABLE V-continued

| Time (min) | Temp. ° C. | TMP-MCF | TMP | Di-TMP | TMP-BMLF | H$_2$O |
|---|---|---|---|---|---|---|
| 17 | 60 | 12.56 | 25.53 | 4.21 | 11.02 | 0.72 |
| 24 | 74 | 16.36 | 26.77 | 4.36 | 8.46 | 0.85 |
| 28 | 80 | 12.76 | 25.91 | 4.23 | 11.62 | 0.79 |
| 59 | 90 | 29.88 | 28.81 | 5.04 | 0.85 | 0.52 |
| 88 | 100 | 31.66 | 29.92 | 4.99 | 0.62 | 0.19 |
| 126 | 112 | 31.80 | 31.71 | 4.51 | 0.73 | 0.12 |
| 138 | 121 | 32.38 | 32.22 | 4.39 | 0.72 | 0.12 |
| 151 | 125 | 32.67 | 32.01 | 4.43 | 0.78 | 0.19 |
| 223 | 125 | 34.8 | 28.71 | 4.04 | 0.78 | 0.36 |
| 283 | 133 | 34.56 | 28.26 | 3.92 | 0.72 | 0.15 |
| 343 | 121 | 34.22 | 27.6 | 3.76 | 0.65 | 0.17 |
| 403 | 126 | 35.39 | 28.11 | 4.06 | 0.76 | 0.11 |

As indicated in the data shown in the foregoing tables of Examples 1–5, an acid treatment tinder the conditions of the invention of a heavy ends residue obtained from the purification of a crude TMP product containing a substantial percentage of TMP-BMLF results in the conversion of the bulk of the TMP-BMLF to TMP and TMP-MCF. A corresponding acid treatment of the heavy ends residue obtained from the purification of a crude TME product results in a similar transformation of the TME-BMLF in such residue to TME and TIME-MCF.

As stated previously, TMP-MCF or TME-MCF in a composition resulting from the process of the invention may be subjected to a transalcoholysis reaction with an excess of a monohydric or dihydric alcohol in the presence of an acid catalyst to produce additional TMP or TME and a valuable acetal by-product. The reaction may be carried out at a temperature, for example, of about 20° C. to about 400° C., preferably about 25° C. to about 300° C. and more preferably about 35° C. to about 210° C., and may be carried out for a period, for example, of about 0 to about 300 minutes, preferably about 60 to about 240 minutes.

The monohydric or dihydric alcohol reacted with TMP-MCF or TME-MCF may contain, for example, 1 to about 6 carbon atoms, such as methanol to produce methylal, ethylene glycol to produce 1,3-dioxolane, 1-propanol to produce di-1-propoxymethane, 2-propanol to produce di-2-propoxymethane, or 2-bromopropanol to produce di-2-bromopropoxymethane, each in addition to TMP or TME. As also mentioned previously, the acid catalyst for this reaction may be any of the strong liquid or solid acid catalysts disclosed as suitable for catalyzing the reaction between TMP-BMLF or TME-BMLF to form TMP-MCF or TME-MCF and additional TMP or TME respectively. The reaction of TMP-MCF with ethylene glycol (EG) to produce 1,3-dioxolane and additional TMP, for example, proceeds in accordance with the following equation:

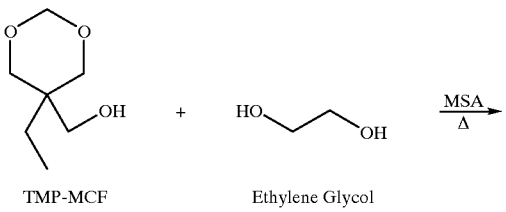

TMP-MCF + Ethylene Glycol $\xrightarrow[\Delta]{MSA}$

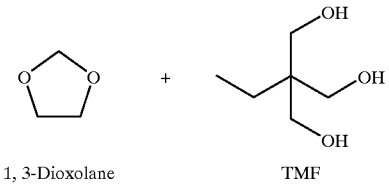

1, 3-Dioxolane + TMF

The amount of monohydric or dihydric alcohol may be in the range, for example, of slightly above the stoichiometric amount necessary to react with TMP-MCF or TME-MCF to produce additional TMP or TME and an acetal by-product, i.e. two moles of a monohydric alcohol or one mole of a dihydric alcohol per mole of TMP-MCF or TME-MCF, or up to about 5–20 fold excess above such stoichiometric amount. The actual amount utilized depends on various factors known to those of skill in the art, for example, the alcohol used, and concentration of reactants in the process stream, among other factors.

The TMP-MCF or TME-MCF reacted with the monohydric or dihydric alcohol may be relatively pure material, such as that obtained by further distilling the TMP-MCF or the TME-MCF containing material obtained by the acid treatment under this invention of the TMP-BMLF or TME-BMLF containing heavy ends residue remaining after the separation of the bulk of the TMP or TME, excess formaldehyde, water and basic condensation agent from the reaction product of n-butyraldehyde or propionaldehyde with formaldehyde. Such a conversion of relatively pure TMP-MCF with ethylene glycol (EG) is illustrated in Example 6.

EXAMPLE 6

To apparatus as described in Examples 1 and 1A was first charged EG (50.5 grams, 0.82 moles), then TMP-MCF (30.25 grams, 0.21 mole) and finally methanesulfonic acid (MSA) as a 70 wt. % solution (0.13 gram, 0.001 mole). Then the reaction was slowly heated to about 205° C.

The composition of the initial charge at room temperature (25.5° C.) before the addition of MSA was found by gas chromatography (GC) to be 1.39 wt. % of H$_2$O, 63.59 wt. % of EG and 36.95 wt. % of TMP-MCF with no detectable quantity of 1,3-dioxolane, TMP or di-TMP. The temperature and composition of withdrawn samples after the addition of MSA at various time intervals, in terms of weight percents of the most significant components determined by GC, are shown in Table VI where "ND" means "not detected."

TABLE VI

| Time (min) | Temp. ° C. | H$_2$O | 1,3-Di-oxolane | EG | TMP-MCF | TMP | Di-TMP |
|---|---|---|---|---|---|---|---|
| 0 | 25.5 | 0.97 | ND | 56.15 | 37.44 | <0.1 | ND |
| 15 | 51.0 | 1.08 | ND | 61.89 | 36.9 | <0.1 | ND |
| 30 | 87.8 | 1.16 | ND | 62.52 | 36.64 | 0.1 | ND |
| 45 | 116.0 | 0.95 | 1.02 | 56.46 | 29.16 | 5.86 | ND |
| 60 | 134.6 | 0.82 | 1.57 | 54.94 | 27.83 | 7.38 | ND |
| 90 | 152.1 | 1.15 | 2.01 | 55.9 | 26.45 | 8.35 | ND |
| 120 | 159.7 | 1.00 | 2.07 | 52.18 | 26.45 | 8.07 | ND |
| 150 | 158.0 | 1.02 | 1.12 | 53.43 | 25.94 | 8.88 | ND |
| 180 | 162.7 | 1.13 | 1.52 | 51.11 | 25.97 | 9.06 | ND |
| 210 | 164.1 | 1.08 | 1.39 | 51.53 | 24.75 | 10.65 | ND |
| 240 | 165.5 | 1.20 | 1.24 | 50.25 | 24.61 | 11.61 | ND |
| 270 | 168.7 | 1.23 | 0.73 | 47.17 | 24.55 | 12.57 | ND |
| 300 | 171.1 | 1.15 | 0.94 | 50.43 | 21.01 | 15.52 | ND |

TABLE VI-continued

| Time (min) | Temp. ° C. | H$_2$O | 1,3-Di-oxolane | EG | TMP-MCF | TMP | Di-TMP |
|---|---|---|---|---|---|---|---|
| 330 | 169.5 | 1.18 | 0.78 | 49.12 | 19.86 | 16.73 | ND |
| 360 | 170.9 | 1.14 | 0.77 | 47.82 | 18.53 | 18.41 | ND |
| 390 | 170.3 | 1.12 | 0.65 | 46.17 | 17.54 | 19.34 | ND |
| 420 | 170.6 | 1.27 | ND | 44.62 | 17.49 | 19.91 | ND |
| 450 | 184.2 | 1.11 | 0.28 | 43.59 | 13.10 | 23.84 | <0.4 |
| 480 | 189.1 | 1.27 | 0.40 | 38.98 | 8.52 | 24.65 | <0.4 |
| 510 | 190.2 | 1.1 | ND | 35.63 | 5.71 | 26.8 | 0.37 |
| 540 | 195.6 | 0.86 | ND | 29.53 | 3.73 | 25.46 | 0.89 |
| 570 | 196.8 | 1.09 | ND | 26.26 | 3.10 | 21.64 | 1.16 |
| 615 | 202.7 | 1.09 | ND | 16.26 | 3.67 | 15.9 | 0.99 |
| 662 | 204.4 | 0.89 | ND | 11.57 | 2.86 | 10.56 | 1.03 |

The reaction solution right after the addition of MSA was colorless. At 150 min. of reaction time the color of the reaction solution was pale yellow. After 180 min. of reaction, the Dean Stark Trap (DST) commenced filling up. At 360 min. the reaction solution was brown.

The Dean Stark Trap (DST) was emptied after 480 min. and the liquid collecting in the DST formed two phases after 510 min. After completion of the reaction, the reaction solution was found by GC to contain 0.92 wt. % of H$_2$O, 9.03 wt. % of EG, 3.34 wt. % of TMP-MCF, 10.59 wt. % of TMP and 0.97 wt. % of di-TMP.

At conclusion, the DST bottom phase weighed 6.72 grams and contained by GC 56.24 wt. % of H$_2$O and 24.56 wt. % of 1,3-dioxolane; and the DST top phase weighed 4.28 grams and contained 3.97 wt. % of H$_2$O and 27.2 wt. % of 1,3-dioxolane, while the DST contents removed after 480 min. reaction time weighed 10.55 grams and contained 13.16 wt. % of H$_2$O and 78.75 wt. % of 1.3-dioxolane.

Based on the GC analysis the total amount of the 1,3-dioxolane collected was 11.12 grams, (0.15 mole). However, based on the water analysis, the amount of 1,3-dioxolane produced was 16.21 grams (0.21 mole). This discrepancy can be in part attributed to the factors used in the GC method. Since there were no other components observed in the gas chromatogram method the accountability based on the water analysis is believed to be more accurate. The amount of TMP left in the reaction mixture at the end of the experiment was determined to be 2.46 crams, (0.018 mole). However, during the course of producing the 1,3-dioxolane, the amount of TMP was found to be 7.42 grams (0.53 mole). The high reaction temperatures readily explain the low amount of TMP formed.

Although the TMP-MCF or the TME-MCF for the foregoing transalcoholysis reaction with a monohydric or dihydric alcohol to produce TMP or TME and an acetal by-product, has been described as obtained by treating the TMP-BMLF or TME-BMLF resulting from the reaction of n-butyraldehyde or propionaldehyde with formaldehyde, to produce TMP or TME, such TMP-MCF or TME-MCF for the transalcoholysis may in fact be obtained from any source.

In the course of purifying the TMP or TME containing TMP-MCF or TME-MCF respectively, obtained as a result of the acid treatment of a TMP-BMLF or TME-BMLF containing residue, a light ends overhead stream is obtained from a distillation finishing treatment of a crude TMP or TME, such light ends containing some TMP or TME as well as a minor amount of TMP-MCF or TME-MCF respectively. However, the latter compounds have been found to be acid washed color forming bodies, i.e., they color the TMP or TME when the latter are subject to contact with an acid in certain applications. While it is relatively easy to separate the TMP-MCF or TME-MCF from the TMP or TME by distillation, this results in some loss of TMP or TME recycled to the system. Thus, in accordance with another aspect of the invention, the light ends overhead stream is subjected to a treatment with an excess of monohydric or dihydric alcohol in the presence of an acid catalyst to transalcoholyze at least some of the TMP-MCF or TME-MCF present in the stream resulting in the formation of additional TMP or TME and a valuable acetal by-product.

The light ends overhead fraction subjected to the transalcoholysis treatment generally contains an amount of TMP or TME, for example, about 70 wt. %, preferably about 50 to about 60 wt. %, and TMP-MCF or TME-MCF in an amount, for example, of about 1–15 wt. % preferably about 2 to about 10 wt. %. The conditions of time and temperature and examples of suitable acid catalysts are the same as those set out previously for the transalcoholysis of relatively pure TMP-MCF or TME-MCF. The transalcoholysis of TMP-MCF in a light ends overhead TMP stream using MSA as catalyst and ethylene glycol (EG) as reacting alcohol is illustrated in Examples 7 and 8.

EXAMPLE 7

Apparatus as described in Examples 1 and 1A was charged with 121.9 grams of a TMP light ends overhead fraction, including 4.15 wt. % of TMP-MCF (5.06 grams, 0.035 mole), 36.55 wt. % of TMP and 0.12 wt. % of H$_2$O, determined by GC, then EG (8.31 grains, 0.13 mole) and finally MSA as a 70% solution (0.201 gram, 0.0002 mole).

Then, the reaction was slowly heated to about 190° C. The temperature and composition in terms of weight percents determined by GC of significant components of samples withdrawn after various time intervals following the addition of MSA, are shown in Table VII where "ND" means "not detected".

TABLE VII

| Time (min) | Temp. ° C. | H$_2$O | EG | TMP-MCF | TMP |
|---|---|---|---|---|---|
| 0 | 26 | 0.28 | ND | 5.42 | 33.09 |
| 15 | 43.7 | 0.34 | <0.21 | 5.87 | 34.02 |
| 30 | 79.3 | 0.06 | 1.97 | 4.08 | 34.60 |
| 45 | 109.7 | 0.44 | <0.21 | 5.22 | 34.01 |
| 60 | 127.2 | 0.42 | <0.21 | 7.99 | 35.27 |
| 90 | 142.5 | 0.52 | 1.77 | 12.20 | 37.00 |
| 120 | 189.9 | 0.60 | <0.21 | 14.55 | 35.98 |
| 150 | 19.2 | 0.72 | 1.37 | 14.69 | 37.89 |
| 180 | 154.7 | 0.58 | ND | 14.19 | 37.50 |
| 210 | 158.5 | 0.66 | 0.26 | 15.07 | 37.70 |
| 240 | 161.7 | 0.86 | 1.39 | 14.43 | 37.22 |
| 270 | 163.9 | 0.90 | 0.63 | 15.16 | 38.13 |
| 300 | 170.1 | 0.78 | <0.21 | 16.14 | 35.93 |
| 330 | 174.9 | 0.75 | <0.21 | 15.25 | 36.66 |
| 360 | 177.4 | 0.77 | 0.21 | 14.87 | 37.23 |
| 390 | 179.2 | 0.83 | <0.21 | 15.99 | 36.98 |
| 423 | 179.2 | 0.08 | 1.40 | 14.38 | 37.38 |
| 450 | 179.7 | 0.83 | <0.21 | 15.75 | 36.98 |
| 480 | 180.4 | 0.73 | <0.21 | 15.3 | 36.23 |
| 510 | 181.2 | 0.75 | <0.21 | 14.72 | 36.38 |
| 540 | 188.2 | 0.46 | <0.21 | 14.64 | 38.57 |

Essentially no 1,3-dioxolane was detected in any of the withdrawn samples. The DS trap started filling with liquid after 120 min., and the liquid collected after reaction completion contained 2.55 wt. % of H$_2$O, 5.74 wt. % of 1,3-dioxolane which was substantially all the 1,3-dioxolane produced in the reaction, and less than 0.21 wt. % of EG, as determined by GC.

At the end of the reaction, based on the water analysis, the amount of 1,3-dioxolane collected in the DS trap was 1.30 grams (0.018 mole). As in Example 6, the discrepancy between the GC and water analysis can be in part attributed to the factors used in the GC method and for similar reasons, the accountability based on the water analysis is believed to be more accurate. The amount of TMP left in the reaction mixture at the end of the experiment increased by 1.03 grams.

EXAMPLE 8

In an attempt to verify and optimize the reaction of the TMP light ends overhead described in the previous example, with EG, the overhead material was spiked with a relatively pure TMP-MCF. Apparatus as described in Examples 1 and 1A was charged with 250.0 grams of TMP light ends overhead containing TMP-MCF (10.38 grams, 0.07 mole), followed by EG (18.10 grams, 0.29 mole) and finally MSA as a 70% solution (0.59 gram, 0.004 mole) and the mixture was slowly heated. When the temperature reached about 150° C. an additional 10.91 grams (0.18 mole) of EG was added and the mixture was then heated to about 207° C. Results obtained in the manner described in Examples 6 and 7 are shown in Table VIII.

TABLE VIII

| Time (min) | Temp. ° C. | $H_2O$ | EG | TMP-MCF | TMP |
|---|---|---|---|---|---|
| 0 | 26.6 | 1.30 | <0.44 | 9.21 | 31.07 |
| 15 | 51 | 0.58 | <0.44 | 9.50 | 32.12 |
| 30 | 83.1 | 0.55 | <0.44 | 10.37 | 32.85 |
| 45 | 112.5 | 0.65 | <0.44 | 16.88 | 34.14 |
| 60 | 136.6 | 0.63 | <0.44 | 18.76 | 36.17 |
| 90 | 153.3 | 0.78 | 0.80 | 17.08 | 36.37 |
| 92 | 150 | 0.73 | <0.44 | 18.54 | 34.11 |
| 105 | 156.6 | 0.88 | 7.51 | 15.44 | 34.41 |
| 120 | 162.2 | 0.93 | <0.44 | 19.95 | 31.51 |
| 135 | 166.3 | 0.99 | 3.83 | 16.67 | 33.25 |
| 150 | 172 | 1.18 | 7.26 | 15.56 | 33.98 |
| 173 | 176.7 | 1.13 | 1.73 | 17.90 | 33.42 |
| 195 | 178 | 1.37 | 0.44 | 18.02 | 32.28 |
| 210 | 179.5 | 1.33 | 5.50 | 15.84 | 33.84 |
| 240 | 189.9 | 1.27 | <0.44 | 19.99 | 33.29 |
| 270 | 203.5 | 1.18 | 0.46 | 16.63 | 32.15 |
| 300 | 205.8 | 1.49 | <0.44 | 17.22 | 28.79 |
| 330 | 204.9 | 1.09 | 3.72 | 15.01 | 31.65 |
| 360 | 204.9 | 1.62 | 2.88 | 13.86 | 27.83 |
| 390 | 204.3 | 0.93 | 2.38 | 13.54 | 28.46 |
| 420 | 205.6 | 0.92 | 3.01 | 12.53 | 27.11 |
| 450 | 206.5 | 0.79 | 0.82 | 12.97 | 25.59 |

The DS trap began filling with liquid after about 60 min. of reaction time and the liquid in the DS trap separated into two phases after about 270 min. Additional EG was added after about 90 min. of reaction time.

The liquid in the bottom or top phase in the DS trap was withdrawn at various temperatures between 203° C. and 207° C. and its weight and weight percent of 1,3-dioxolane and $H_2O$ determined by GC. Results are shown in Table IX.

TABLE IX

|  | $H_2O$ | 1,3-dioxolane | Grams |
|---|---|---|---|
| DS Trap bottom phase removed @ 203° C. | 22.78 | 4.63 | 15.29 |
| DS Trap bottom phase removed @ 205.5° C. | 82.12 | 4.98 | 5.88 |
| DS Trap bottom phase removed @ 204.3° C. | 85.68 | 5.73 | 2.01 |
| DS Trap top phase removed @ 204.3° C. | 2.29 | 8.35 | 16.62 |
| DS Trap bottom phase removed | 85.19 | 6.24 | 2.51 |

TABLE IX-continued

|  | $H_2O$ | 1,3-dioxolane | Grams |
|---|---|---|---|
| @ 206.5° C. |  |  |  |
| DS Trap top phase removed @ 206.5° C. | 2.85 | 8.56 | 4.84 |

Based on the GC analysis, about 3.1 grams (0.04 mole) of 1,3-dioxolane was formed in this example. The results of Examples 7 and 8 indicate that the process of this invention for treating light ends overhead is effective in the production of 1,3-dioxolane by-product and additional TMP indicating a reduction of total TMP-MCF in the system.

In accordance with still another aspect of the invention, the previously described acid treatment of a composition containing a substantial percentage of TMP-BMLF or TME-BMLF, e.g. heavy ends residue containing TMP-BMLF or TME-BMLF, obtained in the course of producing and purifying TMP or TMi by reacting n-butyraldehyde or propionaldehyde with formaldehyde, is carried out in the presence of a monohydric or dihydric alcohol to produce a greater amount of additional TMP or TME than would be obtained by the acid treatment in the absence of the monohydric or dihydric alcohol, and, in addition, an acetal by-product. In some instances, this process can be substituted for, or used in conjunction with the previous described and separately carried out acid treatment of the TMP-BMLF or TME-BMLF containing heavy residue in the absence of monohydric or dihydric alcohol, and the subsequent treatment of a resulting TMP-MCF or the TME-MCF containing stream with the monohydric or dihydric alcohol.

The TMP-BMLF or TME-BMLF containing heavy ends residue and the conditions of the acid treatment, e.g. time, temperature and nature of the acid catalyst are the same as described previously for the acid treatment in the absence of a monohydric or dihydric alcohol, and the nature and amount of excess of the latter alcohol which is added to the heavy ends residue are the same as described previously as suitable for reaction with TMP-MCF or the TME-MCF; note that the stoichiometric amounts of alcohol necessary for complete reaction are at least two moles of a monohydric alcohol or one mole of a dihydric alcohol per mole of TMP-BMLF or TME-BMLF in the residue.

Examples 9 and 10 illustrate the treatment with ethylene glycol (EG) of a TMP-BMLF containing heavy ends residue having the composition shown in Table I as "Initial Feed".

EXAMPLE 9

Apparatus as described in Examples 1 and 1A was charged first with 404.28 grams of heavy ends residue, followed by excess EG (48.0 grams, 0.77 mole), and finally by MSA catalyst as a 70% solution (1.48 gram, 1.08×10-2 mole). Conditions and results obtained in a manner similar to those given in the previous examples, including weight percents determined by GC of various components in withdrawn samples, are shown in Table X where "NR" means "GC analyses not run".

TABLE X

| Time (min) | Temp. ° C. | EG | TMP-MCF | TMP | Di-TMP |
|---|---|---|---|---|---|
| 0 | 63.5 | NR | NR | NR | NR |
| 40 | 97.8 | NR | NR | NR | NR |

TABLE X-continued

| Time (min) | Temp. ° C. | EG | TMP-MCF | TMP | Di-TMP |
|---|---|---|---|---|---|
| 70 | 110 | 5.71 | 29.39 | 32.90 | 3.04 |
| 95 | 118.1 | 4.82 | 30.006 | 33.50 | 2.35 |
| 115 | 123.1 | NR | NR | NR | NR |
| 140 | 127.4 | 3.83 | 29.29 | 32.94 | 2.39 |
| 170 | 131.2 | 2.03 | 29.98 | 33.94 | 2.02 |
| 220 | 139.9 | 4.28 | 29.87 | 33.43 | 2.42 |
| 237 | 143.1 | NR | NR | NR | NR |
| 294 | 153.4 | NR | NR | NR | NR |

Condensation of liquid in the DST commenced at 237 min. and the total liquid in the DST at the end of the experiment separated into two phases, no $H_2O$ or 1,3-dioxolane was detected in any of the withdrawn samples and the entire amounts of these compounds are assumed to have been collected in the DST, the bottom phase of which weighed 12.41 grams and contained by GC determination 73.59 wt. % of $H_2O$, 9.28 wt. % of 1,3-dioxolane, and 2.93 wt. % of TMP-MCF, and the top phase of which weighed 8.69 grams and contained 2.37 wt. % of $H_2O$, 19.64 wt. % of 1,3-dioxolane, and 4.41 wt. % of TMP-MCF.

EXAMPLE 10

The procedure of Example 9 was generally followed except that the charge was 202.14 grams of heavy residue, followed by excess EG (24 grams, 0.39 moles) and finally MSA catalyst as a 70% solution (0.74 grams, 5.38×10-3 moles). Prior to the addition of MSA, at a temperature of 26.7° C., the reaction solution contained, as determined by GC, 22.93 wt. % of EG, 25.71 wt. % of TMP, 4.42 wt. % of di-TMP and 17.75 wt. % of TMP-BMLF. No TMP-MCF was detected. Conditions and result of the reaction are shown in Table XI where "ND" means "not detected by GC".

TABLE XI

| Time (min) | Temp. ° C. | EG | TMP-MCF | TMP | Di-TMP | TMP-BMLF |
|---|---|---|---|---|---|---|
| 0 | 30 | ND | 6.05 | 29.61 | 3.83 | 15.214 |
| 5 | 44 | ND | 5.10 | 30.12 | 3.08 | 12.212 |
| 20 | 47.4 | 24.779 | 4.99 | 25.32 | 2.27 | 5.910 |
| 35 | 89.9 | 2.257 | 15.82 | 30.97 | 2.42 | 5.631 |
| 65 | 105.5 | 5.615 | 29.04 | 33.07 | 3.03 | ND |
| 95 | 120 | 4.113 | 29.58 | 33.52 | 2.51 | ND |
| 125 | 140 | 3.405 | 29.72 | 32.67 | 2.25 | ND |
| 185 | 150 | 4.120 | 30.57 | 30.62 | 2.32 | ND |
| 270 | 168.9 | 3.138 | 36.25 | 31.79 | 2.60 | ND |

Condensation in the DST commenced at 65 min. and liquid was collecting and separating into two phases at 185 min. At the conclusion of the reaction, the DST bottom phase weighed 23.31 grams and contained 10.74 wt. % of 1,3-dioxolane and 3.14 wt. % of TMP-MCF, while the DST top phase weighed 38.73 grams and contained 25.04 wt. % of 1,3-dioxolane and 2.51 wt. % of TMP-MCF. The results of Examples 9 and 10 show that the acid-catalyzed treatment of a TMP heavy ends residue containing TMP-BMLF in the presence of ethylene glycol is effective in producing 1,3-dioxolane by-product and additional TMP and reducing or eliminating the TMP-BMLF in the residue.

We claim:

1. A process comprising contacting a composition containing
    a) a substantial percentage of trimethylolpropane bis-monolinear formal (TMP-BMLF) or trimethylolethane bis-monolinear formal (TME-BMLF),
    b) no more than about 5 wt. % of water, and no more than about 0.5 wt. % of methanol,
    c) with a strong acid catalyst at an elevated temperature and sufficient period of time,
    d) to convert a significant amount of said TMP-BMLF or TME-BMLF to trimethylolpropane (TMP) and trimethylolpropane monocyclic formal (TMP-MCF) or trimethylolethane (TME) and trimethylolethane monocyclic formal (TME-MCF),
        wherein the TMP-MCF or TME-MCF in the composition resulting from such process is subjected to a transalcoholysis reaction with excess monohydric or dihydric alcohol at an elevated temperature and in the presence of an acid catalyst to produce additional TMP or TME respectively and an acetal by-product,
        wherein said composition containing TMP-MCF or TME-MCF is a light ends overhead stream resulting from a finishing treatment of crude TMP or TME.

2. The process of claim 1 wherein said light ends overhead stream contains TMP-MCF and is obtained from a finishing treatment of crude TMP.

3. The process of claim 2 wherein said monohydric or dihydric alcohol contains 1 to about 6 carbon atoms.

4. The process of claim 3 wherein said monohydric or dihydric alcohol is selected from the group consisting of ethylene glycol, methanol, 1-propanol, 2-propanol, and 2-bromopropanol and said acetal by-product is 1,3-dioxolane, methylal, di-1-propoxymethane, di-2-propoxymethane or di-2-bromopropoxymethane respectively.

5. The process of claim 4 wherein said monohydric or dihydric alcohol is ethylene glycol and said acetal by-product is 1,3-dioxolane.

6. The process of claim 1 wherein said light ends contains about 1 to about 15 wt. % of TMP-MCF or TME-MCF.

7. The process of claim 1 wherein said excess of monohydric or dihydric alcohol is about 5–20 fold above the stoichiometric amount of said alcohol necessary to react with the TMP-MCF or TME-MCF.

8. The process of claim 1 wherein said acid catalyst is selected from the group consisting of an alkanesulfonic acid, an arylsulfonic acid, a sulfonated cation-exchange catalyst in acid form, sulfuric acid and phosphoric acid.

9. The process of claim 8 wherein said acid catalyst is methanesulfonic acid.

10. A process comprising subjecting trimethylolpropane monocyclic formal (TMC-MCF) or trimethylolethane monocyclic formal (TME-MCF) to a transalcoholysis reaction with excess monohydric or dihydric alcohol at an elevated temperature and in the presence of an acid catalyst to produce trimethylolpropane (TMP) or trimethylolethane respectively, and an acetal by-product.

11. The process of claim 10 wherein said monohydric or dihydric alcohol contains 1 to about 6 carbon atoms.

12. The process of claim 11 wherein said monohydric or dihydric alcohol is selected from the group consisting of ethylene glycol, methanol, 1-propanol, 2-propanol, and 2-bromopropanol and said acetal by-product is 1,3-dioxolane, methylal, di-1-propoxymethane, di-2-propoxymethane or di-2-bromopropoxymethane respectively.

13. The process of claim 12 wherein said monohydric or dihydric alcohol is ethylene glycol and said acetal by-product is 1,3-dioxolane.

14. The process of claim 10 wherein said excess of monohydric or dihydric alcohol is between about 5–20 fold above the stoichiometric amount of said alcohol necessary to react with the TMP-MCF or TME-MCF.

15. The process of claim 10 wherein said acid catalyst is selected from the group consisting of an alkanesulfonic acid, an arylsulfonic acid, a sulfonated cation-exchange catalyst in acid form, sulfuric acid and phosphoric acid.

16. The process of claim 15 wherein said acid catalyst is methanesulfonic acid.

17. A process comprising contacting a composition containing a substantial percentage of trimethylolpropane bis-monolinear formal (TMP-BMLF) or trimethylolethane bis-monolinear formal (TME-BMLF), no more than about 5 wt. % of water and a monohydric or dihydric alcohol with a strong acid catalyst at an elevated temperature and sufficient period of time to convert a significant amount of said TMP-BMLF or TME-BMLF to trimethylolpropane, respectively, an an acetal by-product.

18. The process of claim 17 wherein said composition is a heavy ends residue obtained by removing the bulk of water, excess formaldehyde, basic condensation agent, and purified TMP or TME in the course of purifying a crude TMP or TME product obtained by reacting n-butyraldehyde or propionaldehyde respectively with formaldehyde in an aqueous medium and in the presence of an alkaline condensation agent.

19. The process of claim 18 wherein said heavy ends residue contains TMP-BMLF and is obtained in the course of purifying a crude TMP product.

20. The process of claim 19 wherein said heavy ends residue contains at least about 10 wt. % of TMP-BMLF.

21. The process of claim 20 wherein said heavy ends residue contains at least about 20 wt. % of TMP-BMLF, and no more than about 1 wt. % of water.

22. The process of claim 17 wherein said elevated temperature is from about 30° C. to about 300° C. and said period of time is from about 2 to about 8 hours.

23. The process of claim 22 wherein said elevated temperature is from about 90° C. to about 220° C. and said period of time is from about 1 to about 6 hours.

24. The process of claim 17 wherein said acid catalyst is an alkanesulfonic acid, an arylsulfonic acid, a sulfonated cation-exchange resin in acid form, sulfuric acid, or phosphoric acid.

25. The process of claim 24 wherein said acid catalyst is selected from the group of sulfuric acid or phosphoric acid.

26. The process of claim 24 wherein said acid catalyst is methanesulfonic acid.

27. The process of claim 24 wherein said acid catalyst is toluenesulfonic acid.

28. The process of claim 24 wherein said acid catalyst is a sulfonated polystyrene-based cation exchange resin in acid form.

29. The process of claim 17 wherein said acid catalyst is present in an amount such that the acidity of the composition is equivalent to that contributed in the range of about 0.1 to about 15 wt. % of methanesulfonic acid.

30. The process of claim 29 wherein said range is about 0.3 to about 1.3 wt. %.

31. The process of claim 19 wherein said heavy ends residue being fed to the process also contain less than about 60 wt. % of TMP.

32. The process of claim 17 wherein said monohydric or dihydric alcohol contains 1 to about 6 carbon atoms.

33. The process of claim 32 wherein said monohydric or dihydric alcohol is selected from the group consisting of ethylene glycol, methanol, 1-propanol, 2-propanol, and 2-bromopropanol and said acetal by-product is 1,3-dioxolane, methylal, di-1-propoxymethyl, di-2-propoxymethane or di-2-bromopropoxymethane respectively.

34. The process of claim 33 wherein said monohydric or dihydric alcohol is ethylene glycol and said acetal by-product is 1,3-dioxolane.

* * * * *